United States Patent
Tuloup et al.

(12)

(10) Patent No.: US 6,326,014 B1
(45) Date of Patent: Dec. 4, 2001

(54) USE OF OXAMATE DERIVATIVES AS DEPIGMENTING AGENTS

(75) Inventors: Remy Tuloup, Paris; Michel Philippe, Wissous, both of (FR)

(73) Assignee: L, Oreal, Paris (FR)

(*) Notice: Subject to any disclaimer, the term of this patent is extended or adjusted under 35 U.S.C. 154(b) by 0 days.

(21) Appl. No.: 09/572,401

(22) Filed: May 16, 2000

Related U.S. Application Data

(63) Continuation of application No. 09/140,532, filed on Aug. 26, 1998, now Pat. No. 6,159,482.

(30) Foreign Application Priority Data

Aug. 26, 1997 (FR) .................................................. 97 10657

(51) Int. Cl.⁷ ....................................................... A61K 7/00
(52) U.S. Cl. ........................... 424/401; 424/62; 424/70.1; 260/465; 514/575; 560/43
(58) Field of Search ............................ 424/62, 407, 70.1; 260/465; 514/575; 560/43

(56) References Cited

U.S. PATENT DOCUMENTS

| | | | |
|---|---|---|---|
| 4,054,591 | * 10/1977 | Klaubert et al. | 260/465 |
| 4,457,872 | 7/1984 | Murase et al. | 260/465 |
| 4,512,987 | * 4/1985 | Schindlery | 514/171 |

FOREIGN PATENT DOCUMENTS

| | | |
|---|---|---|
| 512 257 | 9/1971 | (CH) . |
| 0 712 856 | 5/1996 | (EP) . |
| 0 722 715 | 7/1996 | (EP) . |
| 97/20546 | 6/1997 | (WO) . |

OTHER PUBLICATIONS

A.M. Abdel–Aleem, et al., "Synthesis and antiinflammatory activity of certain new N,N'–oxamides," *Pharmazie*, vol. 35, No. 7, pp. 394–398, (1980).

G.P. Petyunin, et al., "Synthesis and cholagogic activity of substituted amides, arenesulfamides, acyl– and arenesulfo-hydrazides, of 4–hydroxyoxanylic acid," *Khim.–Farm. Zh.*, vol. 18, No. 6, pp. 683–686, (1984).

* cited by examiner

*Primary Examiner*—Thurman K. Page
*Assistant Examiner*—Lakshmi S. Channavajjala
(74) *Attorney, Agent, or Firm*—Oblon, Spivak, McClelland, Maier & Neustadt, P.C.

(57) ABSTRACT

The invention relates to the use of oxamate derivatives in a composition, as agents for depigmenting and/or bleaching human skin, head hair and/or other hairs. The invention also relates to a process for depigmenting and/or bleaching the skin, head hair and/or other hairs, which includes applying a composition comprising oxamate derivatives to human skin, head hair and/or other hairs.

10 Claims, No Drawings

USE OF OXAMATE DERIVATIVES AS DEPIGMENTING AGENTS

This application is a continuation of application Ser. No. 09/140,532 Filed on Aug. 26, 1998, now U.S. Pat. No. 6,159,482.

BACKGROUND OF THE INVENTION

1. Field of the Invention:

The present invention relates to the use of oxamate derivatives as depigmenting or bleaching agents in a cosmetic and/or dermatological composition, and to a depigmenting and/or bleaching composition containing oxamate derivatives.

2. Discussion of the Background

The colour of human skin depends on different factors and, in particular, the seasons of the year, race and sex, and it is mainly determined by the nature and concentration of melanin produced by the melanocytes. Melanocytes are specialized cells which synthesize melanin by means of specific organelles, the melanosomes. In addition, at different periods in their life, certain individuals develop darker and/or more coloured blemishes on the skin and more especially on the hands, making the skin non-uniform. These blemishes are also due to a large concentration of melanin in the keratinocytes at the skin surface.

In the same way, the colour of head hair and other hairs is believed to be due to melanin. When head hair or other hairs are dark, certain people wish to have them lighter. This is particularly advantageous for hairs which are less visible when they are light than when they are dark.

The mechanism for the formation of skin pigmentation, and pigmentation of head hair and other hairs, that is to say the formation of melanin, is particularly complex and, schematically, is believed to involve the following main steps:

Tyrosine→Dopa→Dopaquinone→Dopachrome→Melanin

Tyrosinase (monophenol dihydroxyl phenylalanine: oxygen oxidoreductase EC 1.14.18.1) is the essential enzyme involved in this reaction sequence. It is believed to catalyze the reaction for the conversion of tyrosine into dopa (dihydroxyphenylalanine) by virtue of its hydroxylase activity and the reaction for the conversion of dopa into dopaquinone by virtue of its oxidase activity. This tyrosinase is believed to act only when it is in the mature state, under the action of certain biological factors.

A substance is recognized as being depigmenting if it acts directly on the vitality of the epidermal melanocytes in which melanogenesis takes place and/or if it interferes with one of the steps in the biosynthesis of melanin either by inhibiting one of the enzymes involved in melanogenesis or by becoming intercalated as a structural analogue of one of the chemical compounds in the melanin synthesis chain, whereby this chain may then be blocked and thus ensure the depigmentation.

The substances most commonly used as depigmenting agents are, more particularly, hydroquinone and its derivatives, in particular its ethers such as hydroquinone monomethyl ether and monoethyl ether. Although they have a certain level of efficacy, these compounds are unfortunately not free of side effects on account of their toxicity, which can make them difficult or even hazardous to use. This toxicity arises from the fact that they interfere with fundamental mechanisms of melanogenesis, by killing cells which then risk disrupting their biological environment and which consequently force the skin to eliminate them by producing toxins.

Thus, hydroquinone is a compound which is particularly irritating and cytotoxic to melanocytes, and whose total or partial replacement has been envisaged by many authors.

Substances have thus been sought which are not involved in the mechanism of melanogenesis, but which act upstream on tyrosinase by preventing its activation, and are consequently much less toxic. Kojic acid is commonly used as tyrosinase-activation inhibitor, this acid complexing the copper present in the active site of this enzyme. Unfortunately, this compound can give rise to allergic reactions ("Contact allergy to kojic acid in skin care products", Nakagawa M. et al., in Contact Dermatitis, January 95, Vol 42 (1), pp. 9–13). In addition, this compound is unstable in solution, which somewhat complicates the manufacture of the composition.

It is most particularly sought to use harmless topical depigmenting substances which are of good efficacy, in order to treat regional hyperpigmentations caused by melanocyte hyperactivity, such as idiopathic melasmas, occurring during pregnancy ("pregnancy mask" or chloasma) or during oestro-progestative contraception, localized hyperpigmentations caused by hyperactivity and proliferation of benign melanocytes, such as senile pigmentation marks known as actinic lentigo, accidental hyperpigmentations or depigmentations, possibly due to photosensitization or to post-lesional cicatrization, as well as certain leukodermias, such as vitiligo. For the latter, in which the cicatrizations can result in a scar which gives the skin a whiter appearance and leukodermias), failing being able to repigment the damaged skin, the regions of residual normal skin are depigmented in order to give the skin as a whole a uniform white complexion.

Thus, there is a need for a novel agent for bleaching human skin, hairs and/or head hair which acts as effectively as the known agents, but which does not have their drawbacks, i.e. which is non-irritant, non-toxic and/or non-allergenic to the skin and which is stable in a composition.

SUMMARY OF THE INVENTION

One object of the present invention is to provide a novel agent for bleaching human skin, hairs and/or head hair which acts as effectively as the known agents, but which does not have their drawbacks, i.e. which is non-irritant, non-toxic and/or non-allergenic to the skin and which is stable in a composition.

The Applicant has found, unexpectedly, that certain oxamate derivatives have depigmenting activity, even at low concentrations, without showing any cytotoxicity.

These oxamate derivatives have the formula(I) below:

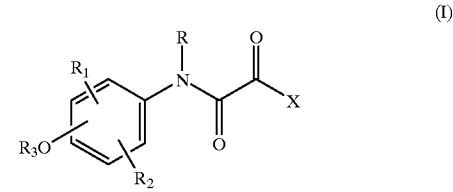

(I)

in which:

R represents a hydrogen atom, a radical chosen from a hydroxyl radical, a radical —OR', a radical —COR', a radical —COOR', a radical —NR'R", a radical —CONR'R", a linear, cyclic or branched, saturated or unsaturated, $C_1$ to $C_{30}$ aliphatic hydrocarbon radical, which is optionally hydroxylated, and a substituted or unsubstituted aryl radical, $R_1$ and $R_2$, which may be identical or different, represent a hydrogen atom, a radical chosen from a hydroxyl radical, a radical —OR', a radical —COR', a radical —COOR', a radical —NR'R", a radical —CONR'R", a radical —SR', —CH$_2$OR', a linear, cyclic or branched, saturated or unsaturated, $C_1$ to $C_{30}$ aliphatic hydrocarbon radical, which is optionally hydroxylated, and a substituted or unsubstituted aryl radical, with R' and R", which may be identical or different, representing a hydrogen atom, a radical chosen from a linear or branched, saturated or unsaturated, $C_1$ to $C_{30}$ aliphatic hydrocarbon radical, which is optionally hydroxylated, and a substituted or unsubstituted aryl radical, an amino acid residue or a sugar residue, $R_3$ represents a hydrogen atom or a radical —COOR$_4$, with $R_4$ representing a linear, cyclic or branched, saturated or unsaturated, $C_1$ to $C_{30}$ aliphatic hydrocarbon or alkoxyl radical, X represents a radical chosen from a radical —OR$_5$, a radical SR$_5$ and a radical —NR$_6$R$_7$, with $R_5$, $R_6$ and $R_7$, which may be identical or different, representing a hydrogen atom, a radical chosen from a linear, cyclic or branched, saturated or unsaturated, $C_1$ to $C_{30}$ aliphatic hydrocarbon radical, which is optionally hydroxylated, and a substituted or unsubstituted aryl radical, an amino acid residue, a peptide residue or a sugar residue.

The subject of the present invention is thus the use of oxamate derivatives of formula (I) in and/or for the manufacture of a cosmetic and/or dermatological composition for depigmenting and/or bleaching human skin and/or for removing skin pigmentation marks and/or depigmenting head hair and/or other hairs.

The subject of the present invention is also the use of these oxamate derivatives in and/or for the manufacture of a cosmetic and/or dermatological composition, as tyrosinase inhibitors and/or as melanin synthesis inhibitors.

The subject of the present invention is also the use of these oxamate derivatives in a cosmetic composition for depigmenting and/or bleaching human skin, head hair or other hairs.

The subject of the present invention is also a cosmetic or dermatological, depigmenting or bleaching composition, characterized in that it contains, in a cosmetically and/or dermatologically acceptable medium, at least one oxamate derivative of formula (I) as described above. This composition is more particularly intended for topical use on the skin and/or its exoskeleton (head hair, other hairs and the nails).

The present invention also relates to a cosmetic and/or dermatological process for depigmenting and/or bleaching human skin, head hair or other hairs, which includes applying a composition according to the invention to the skin, head hair or other hairs.

The composition according to the invention is suitable for topical use and thus contains a cosmetically or dermatologically acceptable medium, i.e. one which is compatible with the skin, head hair or other hairs.

DESCRIPTION OF THE PREFERRED EMBODIMENTS

Other features of the invention will become apparent in the course of the following description of exemplary embodiments, which are given for illustration of the invention and are not intended to be limiting.

These compounds are known in particular as intermediates for particular compounds having anti-inflammatory activity (Pharmacie, 35(7), 394–8, 1980), for their polymer-stabilizing properties (EP 0,511,166) or for biological activities, such as neuraminidase-inhibitory activity (Hoppe-Seyler's Physiol. Chem., 358(3), 391–6, 1977) or cholagogic activity (Khim-Farm. Zh., 18(6), 683–6, 1984), the entire contents of each of which are hereby incorporated by reference.

These oxamate compounds are thus already described, in particular, in the documents cited above. They have the advantage of being easy to obtain from simple precursors, such as oxalyl halides, oxamide or oxamic acid esters.

According to the present invention, among the linear or branched aliphatic hydrocarbon radicals having from 1 to 30 carbon atoms, mention may be made advantageously of methyl, ethyl, propyl, isopropyl, butyl, tert-butyl, hexyl, octyl, nonyl, 2-ethylhexyl and dodecyl radicals. Preferably, these radicals have from 1 to 12 carbon atoms. Even more preferably, the aliphatic hydrocarbon radical generally comprises from 1 to 6 carbon atoms. As lower aliphatic hydrocarbon radicals, mention may be made of methyl, ethyl, propyl, isopropyl, tert-butyl and hexyl radicals.

Among the linear aliphatic hydrocarbon radicals having from 1 to 30 carbon atoms, mention may be made in particular of methyl, ethyl, propyl, 2-ethylhexyl, octyl, dodecyl, hexadecyl and octadecyl radicals.

Among the branched aliphatic hydrocarbon radicals having from 1 to 30 carbon atoms, mention may be made in particular of 2-methylbutyl, 2-methylpentyl, 1-methylhexyl and 3-methylheptyl radicals.

When it is unsaturated, the radical preferably has one or more ethylenic unsaturations, more particularly such as an allyl radical.

When the aliphatic hydrocarbon radical is cyclic, mention may be made in particular of the cyclohexyl, cholesteryl or tert-butylcyclohexyl radical.

When it is hydroxylated, the radical preferably comprises 1 to 6 carbon atoms and 1 to 5 hydroxyl groups.

Among the monohydroxyalkyl radicals, the preferred radical preferably contains 1 or 3 carbon atoms, in particular the hydroxymethyl, 2-hydroxyethyl or 2- or 3-hydroxypropyl radicals.

Among the polyhydroxyalkyl radicals, the preferred radical has from 3 to 6 carbon atoms and from 2 to 5 hydroxyl groups, such as the 2,3-dihydroxypropyl, 2,3,4-trihydroxybutyl or 2,3,4,5-tetrahydroxypentyl radicals or the pentaerythritol residue.

The alkoxylated radicals are aliphatic hydrocarbon radicals, in particular such as those described above, preceded by an oxygen atom.

Among the aryl radicals, a phenyl, thiophene or pyridine radical, optionally substituted with at least one halogen atom, a hydroxyl radical, an alkyl radical, a nitro function, a methoxy group or an optionally substituted amine function is preferred. An optionally substituted phenyl radical is preferred.

The term sugar residue is understood to refer to a residue derived in particular from glucose, galactose or mannose, or alternatively from glucuronic acid.

The term amino acid residue is understood to refer in particular to a residue derived from one of the amino acids, such as lysine, glycine or aspartic acid, and the term peptide residue is understood to refer more particularly to a dipeptide or tripeptide residue resulting from the combination of amino acids.

Preferably, the oxamate derivatives used in the present invention are those for which at least one, and preferably all, of the following conditions are satisfied:

$R_3$ represents a hydrogen atom, the function —$OR_3$ on the phenyl radical is in an ortho position or, advantageously, in the para position, R is a hydrogen atom or a linear or branched, $C_1$–$C_{24}$ aliphatic hydrocarbon radical, which is optionally unsaturated or hydroxylated, X is a radical —$OR_5$, advantageously with $R_5$ representing a hydrogen atom or a linear or branched $C_1$–$C_{24}$ aliphatic hydrocarbon radical, which is optionally unsaturated or hydroxylated, or X is a radical —$NR_6R_7$ advantageously with $R_6$ and $R_7$, which may be identical or different, representing a hydrogen atom, a linear or branched $C_1$–$C_{24}$ aliphatic hydrocarbon radical, which is optionally unsaturated or hydroxylated, an amino acid residue, a peptide residue or a sugar residue.

The subject of the present invention is also the use of these oxamate derivatives in and/or for the manufacture of a cosmetic and/or dermatological composition, as tyrosinase inhibitors and/or as melanin synthesis inhibitors.

The subject of the present invention is also the use of these oxamate derivatives in a cosmetic composition for depigmenting and/or bleaching human skin, head hair or other hairs.

The subject of the present invention is also a cosmetic or dermatological, depigmenting or bleaching composition, characterized in that it contains, in a cosmetically and/or dermatologically acceptable medium, at least one oxamate derivative of formula (I) as described above. This composition is more particularly intended for topical use on the skin and/or its exoskeleton (head hair, other hairs and the nails).

The present invention also relates to a cosmetic and/or dermatological process for depigmenting and/or bleaching human skin, head hair or other hairs, which consists in applying a composition according to the invention to the skin, head hair or other hairs.

The composition according to the invention is suitable for topical use and thus contains a cosmetically or dermatologically acceptable medium, i.e. one which is compatible with the skin, head hair or other hairs.

The oxamate derivatives of formula (I) can be present in the composition in an amount ranging from 0.001 to 10% and preferably from 0.005 to 5%, and most preferably 0.01 to 5% of the total weight of the composition.

The composition of the invention may be in any pharmaceutical form normally used for topical application, in particular in the form of an aqueous, aqueous-alcoholic or oily solution, an oil-in-water or water-in-oil or multiple emulsion, an aqueous or oily gel, a liquid, pasty or solid anhydrous product, a dispersion of oil in an aqueous phase with the aid of spherules, these spherules possibly being polymeric nanoparticles such as nanospheres and nanocapsules or better still lipid vesicles of ionic and/or non-ionic type.

This composition may be relatively fluid and have the appearance of a white, clear, or coloured cream, an ointment, a milk, a lotion, a serum, a paste or a foam. It may optionally be applied to the skin or to the hair in aerosol form. It may also be in solid form and, for example, in the form of a stick. It can be used as a care product and/or as a make-up product. It can also be in the form of a shampoo or a conditioner.

In a known manner, the composition of the invention can also contain the usual adjuvants in the cosmetics and dermatological fields, such as hydrophilic or lipophilic gelling agents, hydrophilic or lipophilic active agents, preserving agents, antioxidants, solvents, fragrances, fillers, sunscreens, pigments, odour absorbers and dyestuffs. The amounts of these various adjuvants are those used conventionally in the fields considered, and, for example, from 0.01 to 20%, preferably 0.1 to 15%, and more preferably 1 to 10% of the total weight of the composition. Depending on their nature, these adjuvants can be introduced into the fatty phase, into the aqueous phase, into lipid vesicles and/or into nanoparticles.

When the composition of the invention is an emulsion, the proportion of the fatty phase can range from 5 to 80% by weight, and preferably from 5 to 50% by weight, and more preferably 10 to 30% by weight, relative to the total weight of the composition. The oils, the emulsifiers and the co-emulsifiers used in the composition in emulsion form are chosen from those used conventionally in the field considered. The emulsifier and the co-emulsifier are present in the composition in a proportion ranging from 0.3 to 30% by weight, and preferably from 0.5 to 20% by weight, relative to the total weight of the composition.

As oils which can be used in the invention, mention may be made of mineral oils (liquid petroleum jelly), oils of plant origin (avocado oil, soybean oil), oils of animal origin (lanolin), synthetic oils (perhydrosqualene), silicone oils (cyclomethicone) and fluoro oils (perfluoropolyethers). Fatty alcohols (cetyl alcohol), fatty acids and waxes (carnauba wax, ozokerite) can also be used as fatty substances.

As emulsifiers and co-emulsifiers which can be used in the invention, mention may be made, for example, of fatty acid esters of polyethylene glycol, such as PEG-20 stearate, and fatty acid esters of glycerol, such as glyceryl stearate.

As hydrophilic gelling agents, mention may be made in particular of carboxyvinyl polymers (carbomer), acrylic copolymers such as acrylate/alkylacrylate copolymers, polyacrylamides, polysaccharides, natural gums and clays, and, as lipophilic gelling agents, mention may be made of modified clays such as bentones, metal salts of fatty acids, hydrophobic silica and polyethylenes.

Polyols (glycerol, propylene glycol), vitamins, keratolytic agents and/or desquamating agents (salicylic acid and its derivatives, α-hydroxy acids, ascorbic acid and its derivatives), anti-inflammatory agents, calmants and mixtures thereof can be used in particular as active agents. The oxamate derivatives can also be combined with other depigmenting agents, such as kojic acid or hydroquinone and its derivatives, which allows these derivatives to be used at doses that are less toxic to the skin. In the event of incompatibility, these active agents and/or the oxamate derivatives can be incorporated into spherules, in particular ionic or non-ionic vesicles and/or nanoparticles (nanocapsules and/or nanospheres), so as to isolate them from each other in the composition.

EXAMPLES

Having generally described the invention, a further understanding can be obtained by reference to contain specific examples, which are provided for purposes of illustration only and are not intended to be limiting unless otherwise specified. The concentrations are given as percentages by weight.

Example 1

Ethyl N-(4-hydroxyphenyl)oxamate 250 g of para-aminophenol in one liter of ethyl oxylate are maintained at 120° C. for 4 hours. After cooling, one liter of absolute ethanol is added to the reaction mixture and the resulting mixture is cooled to 0° C. The ethyl N-(4- hydroxyphenyl)oxamate precipitates out and is filtered off, washed with heptane and then dried under vacuum. The yield is 91%.

Example 2

N-(4-hydroxyphenyl)-N'-(D-glucamino)oxamide 2 g of D-glucamine and 2 g of ethyl N-(4-hydroxyphenyl) oxamate are refluxed in 50 cm³ of ethanol for 3 hours. The medium is then cooled to 0° C. The expected oxamide precipitates out in a yield of 50%.

Tests:

A biological test demonstrated the depigmenting activity of the oxamate derivatives of formula (I).

This test corresponds to the one described in patent FR 2,734,825 filed by the Applicant, as well as in the article by R. Schmidt, P. Krien and M. Régnier, Anal. Biochem., 235(2), 113–18, (1996), the entire contents of each of which are hereby incorporated by reference. This test is thus carried out on a co-culture of keratinocytes and melanocytes.

For each test compound, the $IC_{50}$ value, which corresponds to the micromolar concentration ($\mu M$) for which a 50% inhibition of melanogenesis is observed, is determined.

Moreover, a class is given to each of these compounds as regards their maximum depigmenting activity:

class 1: 10 to 30% inhibition of melanogenesis relative to the control (same experiment without test compound);
class 2: 30 to 60% inhibition of melanogenesis relative to the control (same experiment without test compound);
class 3: 60 to 100% inhibition of melanogenesis relative to the control (same experiment without test compound).

The results are collated in Table (I) below.

|  | $IC_{50}$ ($\mu M$) | Class |
| --- | --- | --- |
| Compound of Example 1 | 10 | 3 to 50 $\mu M$ |
| Compound of Example 2 | 10 | 2 to 10 $\mu M$ |
| Kojic acid | 500 | 2 to 500 $\mu M$ |

These compounds of formula (I) thus have greater depigmenting efficacy than kojic acid. In addition, they have the advantage of showing no cytotoxicity towards keratinocytes and melanocytes, which is a major defect of the existing depigmenting agents.

EXAMPLES OF COMPOSITIONS

Example 3

Treating Cream

| Cetyl alcohol | 1.05% |
| --- | --- |
| PEG-20 stearate (Myrj 49 sold by the company ICI) | 2% |
| Cyclomethicone | 6% |
| Compound of Example 1 | 0.5% |
| Carbomer | 0.6% |
| Glycerol | 3% |
| Triethanolamine | 1% |
| Preserving agents | 0.5% |
| Demineralized water qs | 100% |

When applied daily, the cream obtained allows the skin to be bleached.

Example 4

Treating Gel

| Propylene glycol | 10% |
| --- | --- |
| Ethyl alcohol | 40% |
| Glycerol | 3% |
| Compound of Example 2 | 0.5% |
| Preserving agents | 0.15% |
| Fragrance | 0.15% |
| Demineralized water qs | 100% |

The gel obtained can be used daily and is capable of depigmenting the skin.

Example 5

Treating Stick

| Carnauba wax | 5% |
| --- | --- |
| Ozokerite | 7% |
| Lanolin | 6% |
| Titanium dioxide (pigments) | 20% |
| Rice starch (filler) | 7% |
| EDTA | 0.1% |
| Compound of Example 1 | 2% |
| Perhydrosqualene qs | 100% |

When used on pigmentation marks, the stick obtained allows these marks to be attenuated, or even makes them disappear altogether.

This application is based on French patent application FR 9710657, filed Aug. 26, 1997, the entire contents of which are hereby incorporated by reference.

Obviously, numerous modification and variations of the present invention are possible in light of the above teachings. It is therefore to be understood that, within the scope of the appended claims, the invention may be practiced otherwise than as specifically described herein.

What is claimed as new and desired to be secured by Letters Patent in the United States is:

1. A skin and/or its exoskeleton, depigmenting or bleaching composition in a form suitable for topical application to the skin and/or its exoskeleton, comprising, in an amount of 0.001 to 10% of the total weight of the composition, of at least one oxamate of formula (I):

$$\text{(I)}$$

wherein

R represents a hydrogen atom or a radical selected from the group consisting of a hydroxyl radical, a radical —OR', a radical —COR', a radical —COOR', a radical —NR'R'', a radical —CONR'R'', a linear, cyclic or branched, saturated or unsaturated, optionally hydroxylated, $C_1$ to $C_{30}$ aliphatic hydrocarbon radical, and a substituted or unsubstituted aryl radical, $R_1$ and $R_2$, which may be identical or different, represent a hydrogen atom or a radical selected from the group consisting of a hydroxyl radical, a radical —OR', a radical —COR', a radical —COOR', a radical —NR'R", a radical —CONR'R", a radical —SR', —CH$_2$OR', a linear, cyclic or branched, saturated or unsaturated, optionally hydroxylated, C$_1$ to C$_{30}$ aliphatic hydrocarbon radical, and a substituted or unsubstituted aryl radical, wherein R' and R", which may be identical or different, represent a hydrogen atom, a radical selected from the group consisting of a linear or branched, saturated or unsaturated, optionally hydroxylated, C$_1$ to C$_{30}$ aliphatic hydrocarbon radical, and a substituted or unsubstituted aryl radical, an amino acid residue or a sugar residue, R$_3$ represents a hydrogen atom or a radical —COOR$_4$, wherein R$_4$ represents a linear, cyclic or branched, saturated or unsaturated C$_1$ to C$_{30}$ aliphatic hydrocarbon or alkoxyl radical, X represents a radical selected from the group consisting of a radical —OR$_5$, a radical —SR$_5$ and a radical —NR$_6$R$_7$, wherein R$_5$, R$_6$ and R$_7$, which may be identical or different, represent a hydrogen atom, a radical selected from the group consisting of a linear, cyclic or branched, saturated or unsaturated, optionally hydroxylated, C$_1$ to C$_{30}$ aliphatic hydrocarbon radical, and a substituted or unsubstituted aryl radical, an amino acid residue, a peptide residue or a sugar residue;

at least one active agent selected from the group consisting of keratolytic agents, desquamating agents, anti-inflammatory agents, calmants, depigmenting agents and mixtures thereof; and a cosmetically or dermatologically acceptable medium.

2. The composition of claim 1, wherein

R$_3$ represents a hydrogen atom,

—OR$_3$ is in the ortho or the para position,

R is a hydrogen atom or a linear or branched, optionally unsaturated or hydroxylated, C$_1$–C$_{30}$ aliphatic hydrocarbon radical, X is a radical —OR$_5$, wherein R$_5$ represents a hydrogen atom or a linear or branched, optionally unsaturated or hydroxylated, C$_1$–C$_{30}$ aliphatic hydrocarbon radical, or X is a radical —NR$_6$R$_7$, wherein R$_6$ and R$_7$, which may be identical or different, represent a hydrogen atom, a linear or branched C$_1$–C$_{30}$ aliphatic hydrocarbon radical, optionally unsaturated or hydroxylated, an amino acid residue, a peptide residue or a sugar residue.

3. The composition of claim 1, wherein the oxamate is present in an amount of 0.005 to 5% of the total weight of the composition.

4. The composition of claim 1 additionally containing an adjuvant in an amount of 0.01 to 20% of the total weight of the composition.

5. The composition of claim 1 in the form of an emulsion.

6. The composition of claim 1 in the form of an aqueous composition.

7. The composition of claim 1 in the form of a cream.

8. The composition of claim 1 in the form of a gel.

9. The composition of claim 1 in the form of a stick.

10. A skin and/or its exoskeleton, depigmenting or bleaching composition, in the form of a stick and in a form suitable for topical application to the skin and/or its exoskeleton, comprising at least one oxamate of formula (I):

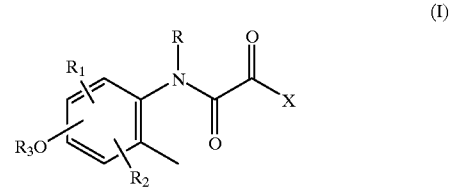

(I)

wherein

R represents a hydrogen atom or a radical selected from the group consisting of a hydroxyl radical, a radical —OR', a radical —COR', a radical —COOR', a radical —NR'R", a radical —CONR'R", a linear, cyclic or branched, saturated or unsaturated, optionally hydroxylated, C$_1$ to C$_{30}$ aliphatic hydrocarbon radical, and a substituted or unsubstituted aryl radical, R$_1$ and R$_2$, which may be identical or different, represent a hydrogen atom or a radical selected from the group consisting of a hydroxyl radical, a radical —OR', a radical —COR', a radical —COOR', a radical —NR'R", a radical —CONR'R", a radical —SR', —CH$_2$OR', a linear, cyclic or branched, saturated or unsaturated, optionally hydroxylated, C$_1$ to C$_{30}$ aliphatic hydrocarbon radical, and a substituted or unsubstituted aryl radical, wherein R' and R", which may be identical or different, represent a hydrogen atom, a radical selected from the group consisting of a linear or branched, saturated or unsaturated, optionally hydroxylated, C$_1$ to C$_{30}$ aliphatic hydrocarbon radical, and a substituted or unsubstituted aryl radical, an amino acid residue or a sugar residue, R$_3$ represents a hydrogen atom or a radical —COOR$_4$, wherein R$_4$ represents a linear, cyclic or branched, saturated or unsaturated C$_1$ to C$_{30}$ aliphatic hydrocarbon or alkoxyl radical, X represents a radical selected from the group consisting of a radical —OR$_5$, a radical —SR$_5$ and a radical —NR$_6$R$_7$, wherein R$_5$, R$_6$ and R$_7$, which may be identical or different, represent a hydrogen atom, a radical selected from the group consisting of a linear, cyclic or branched, saturated or unsaturated, optionally hydroxylated, C$_1$ to C$_{30}$ aliphatic hydrocarbon radical, and a substituted or unsubstituted aryl radical, an amino acid residue, a peptide residue or a sugar residue; and a cosmetically or dermatologically acceptable medium.

* * * * *